(12) United States Patent
Michelson

(10) Patent No.: US 7,637,951 B2
(45) Date of Patent: Dec. 29, 2009

(54) NESTED INTERBODY SPINAL FUSION IMPLANTS

(75) Inventor: Gary K. Michelson, Venice, CA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 10/246,931

(22) Filed: Sep. 19, 2002

(65) Prior Publication Data

US 2003/0023307 A1    Jan. 30, 2003

Related U.S. Application Data

(62) Division of application No. 09/566,272, filed on May 5, 2000, now Pat. No. 6,485,517.

(60) Provisional application No. 60/132,665, filed on May 5, 1999.

(51) Int. Cl.
*A61F 2/44* (2006.01)
(52) U.S. Cl. .................................................. 623/17.11
(58) Field of Classification Search ... 623/17.11–17.16, 623/FOR. 17
See application file for complete search history.

(56) References Cited

U.S. PATENT DOCUMENTS

| | | | |
|---|---|---|---|
| 3,426,364 A | 2/1969 | Lumb | |
| 3,875,595 A | 4/1975 | Froning | |
| 4,349,921 A | 9/1982 | Kuntz | |
| 4,501,269 A | 2/1985 | Bagby | |
| RE31,865 E | 4/1985 | Roux | |
| 4,599,086 A | 7/1986 | Doty | |
| 4,636,217 A | 1/1987 | Ogilvie et al. | |
| 4,714,469 A | 12/1987 | Kenna | |
| 4,743,256 A | 5/1988 | Brantigan | |
| 4,759,769 A | 7/1988 | Hedman et al. | |
| 4,820,305 A | 4/1989 | Harms et al. | |
| 4,877,020 A | 10/1989 | Vich | |
| 4,878,915 A | 11/1989 | Brantigan | |
| 4,904,261 A | 2/1990 | Dove et al. | |
| 4,955,908 A | 9/1990 | Frey et al. | |
| 4,961,740 A | 10/1990 | Ray et al. | |

(Continued)

FOREIGN PATENT DOCUMENTS

DE    35 05567 A1    5/1986

(Continued)

OTHER PUBLICATIONS

Crock, H.V.; Practice of Spinal Surgery; Springer-Verlag/Wien, New York (1983), pp. 75-85.

(Continued)

*Primary Examiner*—David H. Willse
(74) *Attorney, Agent, or Firm*—Martin & Ferraro, LLP

(57) ABSTRACT

Tapered root threaded hollow perforated interbody spinal fusion implants are disclosed for placement into a disc space in a human spine between adjacent vertebral bodies. The implants have opposite arcuate portions with lockable screws passing therethrough for engaging each of the adjacent vertebral bodies. The implants are adapted for use in side-by-side pairs such that a portion of the circumference of a first implant nests within the circumference of a second implant, so as to have a reduced combined width.

118 Claims, 9 Drawing Sheets

U.S. PATENT DOCUMENTS

| | | | |
|---|---|---|---|
| 5,015,247 A | 5/1991 | Michelson |
| 5,026,373 A | 6/1991 | Ray et al. |
| 5,055,104 A | 10/1991 | Ray |
| 5,258,031 A | 11/1993 | Salib et al. |
| 5,397,364 A | 3/1995 | Kozak et al. |
| 5,425,772 A | 6/1995 | Brantigan |
| 5,458,638 A | 10/1995 | Kuslich et al. |
| 5,484,437 A | 1/1996 | Michelson |
| 5,489,307 A | 2/1996 | Kuslich et al. |
| 5,489,308 A | 2/1996 | Kuslich et al. |
| 5,534,031 A | 7/1996 | Matsuzaki et al. |
| 5,571,109 A | 11/1996 | Bertagnoli |
| 5,593,409 A | 1/1997 | Michelson |
| 5,609,636 A | 3/1997 | Kohrs et al. |
| 5,645,598 A | 7/1997 | Brosnahan, III |
| 5,658,337 A | 8/1997 | Kohrs et al. |
| 5,669,909 A | 9/1997 | Zdeblick et al. |
| 5,683,463 A | 11/1997 | Godefroy et al. |
| 5,741,253 A | 4/1998 | Michelson |
| 5,766,252 A | 6/1998 | Henry et al. |
| 5,782,919 A | 7/1998 | Zdeblick et al. |
| D397,439 S | 8/1998 | Koros et al. |
| 5,800,547 A | 9/1998 | Schäfer et al. |
| 5,800,550 A | 9/1998 | Sertich |
| 5,814,084 A | 9/1998 | Grivas et al. |
| 5,861,041 A | 1/1999 | Tienboon |
| 5,904,719 A | 5/1999 | Errico et al. |
| 6,033,438 A | 3/2000 | Bianchi et al. |
| 6,080,155 A | 6/2000 | Michelson |
| 6,120,503 A | 9/2000 | Michelson |
| 6,206,922 B1 | 3/2001 | Zdeblick et al. |
| 6,210,412 B1 | 4/2001 | Michelson |
| 6,224,631 B1 | 5/2001 | Kohrs |
| 6,241,770 B1 | 6/2001 | Michelson |
| 6,923,810 B1 | 8/2005 | Michelson |
| 7,534,254 B1 | 5/2009 | Michelson |

FOREIGN PATENT DOCUMENTS

| | | |
|---|---|---|
| EP | 0 179 695 A1 | 4/1986 |
| EP | 0599419 A2 | 6/1994 |
| EP | 0 637 440 B1 | 10/1997 |
| ES | 283078 | 5/1985 |
| JP | 5-269160 | 10/1993 |
| WO | WO 96/40020 | 12/1996 |
| WO | WO 98/55052 | 12/1998 |

OTHER PUBLICATIONS

Bagby, G.W.; Arthrodesis by the Distraction-Compression Method Using a Stainless Steel Implant; Orthopedics, vol. II, No. 6, pp. 931-934 (Jun. 1987).

Laparoscopic Bone Dowel Surgical Technique; Brochure of Sofamor Danek (1995), 17 pages.

Brochure of University of Florida Tissue Bank; MD-I and MD-II Custom Machine Cortical Dowels; (*Circa* 1996), 3 pages.

Brochure of University of Florida Tissue Bank; MD-III Threaded Cortical Dowel; (Circa 1996), 2 pages.

Glazer, P.A., et al.; Biomechanical Analysis of Multilevel Fixation Methods in the Lumbar Spine; Spine, vol. 22, No. 2, pp. 171-182 (1997).

Ray, C.D.; Spinal Interbody Fusions: A Review, Featuring New Generation Techniques; Neurosurgery Quarterly, 7(2):135-156 (1997).

A picture of a Medtronic, Sofamor Danek Display; titled "Evolving With Your Needs" (Apr. 6, 2000), 1 page.

International Search Report mailed Aug. 14, 2000 from corresponding International PCT Application No. PCT/US00/12363, filed May 5, 2000.

NESTED INTERBODY SPINAL FUSION IMPLANTS

RELATED APPLICATION

This is a divisional of application Ser. No. 09/566,272, filed May 5, 2000, now U.S. Pat. No. 6,485,517, which claims the benefit of U.S. provisional application No. 60/132,665, filed May 5, 1999, all of which are incorporated herein by reference.

BACKGROUND OF THE INVENTION

Description of the Related Art

The use of hollow threaded perforated interbody spinal fusion implants such as taught by U.S. Pat. No. 5,015,247 to Michelson ('247), incorporated by reference herein, is now commonplace. Nevertheless, because of the structure and biomechanical properties of these implants, the use of such implants has not been available for all patients requiring spinal fusion, but rather has been limited to a subset of that population. While such implants have proven to be very successful when used correctly, such success has not been universal.

A previously identified problem as discussed in U.S. Pat. No. 4,593,409 to Michelson ('409), incorporated by reference herein, is the frequent need for such implants to have a reduced combined width relative to their combined height. This permits the height, which is usually the implant diameter, to be sufficiently great so as to span the height of the distracted disc space and adequately penetrate and engage each of the vertebral bodies adjacent that disc space, and yet have a significantly lesser width so that when such implants are utilized in side-by-side pairs, the combined width is such that the paired implants do not protrude beyond the width of the spine. Historically, this not infrequent situation has deprived many patients needing spinal fusion from use of the prior art technology as implants of the desired height could not safely be placed within that patient's disc space because of the width problem. Alternatively, downsized versions of these implants were implanted with poor results as the implants were of insufficient size to adequately function for their intended purpose.

As discussed in Michelson '409, implants having various vertebral bone engaging surface projections have the advantage of enhanced stability within the spine as compared to an implant having a smooth surface. The use of a thread or thread portions has proven particularly beneficial and have been described in Michelson '247. As described in Michelson's co-pending application Ser. Nos. 08/484,928; 08/480,904; and 08/480,908 incorporated by reference herein, similar devices in which opposite vertebrae engaging arcuate surfaces are in angular relationship to each other may be useful to be fuse the vertebrae in a more lordotic angular relationship relative to each other. Implants of the related art are taller near the end adapted to be placed proximate the anterior aspect of the vertebral bodies than at the opposite end adapted to be placed proximate the posterior aspect of vertebral bodies. The related art implants are generally wedge-shaped when viewed from the side. The wedged configuration causes the implant to be less stable within the spine than if it were non-wedged. Further limiting the stability of these implants, compromising the surface area available for contact and fusion, and limiting the volume of osteogenic material containable within the implants is a result of the fact that these implants have generally been relatively flat across their trailing ends so as to be rotationally symmetrical about their mid-longitudinal axes.

The anterior aspects of the vertebral bodies are generally curved from side-to-side. As a result, related art implants needed to be rather deeply inset into the disc space and away from the anterior aspects of the vertebral bodies so as to prevent the implants from protruding from the disc space at their lateral wall and trailing end junctions, wheresuch a protrusion of the implant could place vital structures adjacent the spine at risk.

There is, therefore, a need for further improvement in the design of such interbody spinal fusion implants so as to firstly extend their range of usefulness, and secondly to further increase the rate of success when such implants are used.

SUMMARY OF THE INVENTION

In accordance with the present invention, as embodied and broadly described herein, there are provided interbody spinal fusion implants that are threaded at least in part and require an element of rotation for insertion across a disc space between two adjacent vertebral bodies of a spine. The implants of the present invention are configured to be positioned in close proximity to each other such that the combined width of the implants is less than the combined height of the implants. The implants preferably have a leading end, a trailing end opposite the leading end, and a mid-longitudinal axis and length therebetween. The implants preferably have opposite arcuate portions adapted for placement toward and at least in part within the adjacent vertebral bodies and have a distance therebetween defining an implant height greater than the normal height of the disc space to be fused. Each of the opposite arcuate portions preferably has at least one opening in communication with each other for permitting for the growth of bone from vertebral body to adjacent vertebral body through the implant. Preferably, at least a portion of a thread is formed on the exterior of each of the opposite arcuate portions for penetrably engaging the adjacent vertebral bodies and to facilitate securing the implant into the spine by at least in part rotating the implant about its mid-longitudinal axis. At least a first one of the implants preferably has a lateral side wall and a medial side wall with a distance therebetween defining an implant width transverse to the implant height. The width of the first implant is less than its height along at least a portion of its length. The medial side wall of the first implant is preferably configured to be positioned in close proximity to at least a second spinal implant such that the combined width of the first and second implants is less than the combined height of those implants.

The present invention provides for improved interbody spinal fusion implants for placement within the spine in longitudinal side-by-side nested pairs. As used herein, the terms "nesting or nested" refer to the placement of at least two implants in side-by-side relationship and close proximity to each other. In a preferred embodiment, the present invention teaches the nesting together of a pair of tapered root threaded spinal fusion implants, such that the nested implant pair has a combined reduced width relative to the combined height of the individual implants. As used herein, the terms "tapered root" refers to an implant having an outer diameter as measured at the peaks of the bone penetrating protrusions, such as threads, and a root diameter, wherein the root diameter tapers from one end to the other end of the implant.

An embodiment of the present invention includes an interbody spinal fusion implant adapted to receive along its length a second circumferentially threaded complimentary interbody spinal fusion implant, such that the second implant nests within the circumference of the first implant. The nested longitudinal side-by-side pair has a combined width less than the implants' combined maximum diameters, which maximum diameters generally define the over-all implant heights. In a further embodiment, the implants of the present invention are angled toward each other such that the combined width at the leading ends is further lessened.

The present invention implants have opposite arcuate portions and preferably are rotated into place. In an embodiment of the present invention, the implants may be generally cylindrical and have a thread or thread portions. In a preferred embodiment, the root diameter of the implant is generally conical or a portion of cone in that the opposite arcuate surfaces for contacting the vertebrae adjacent the disc space are in angular relationship to each other generally over the length of the implants. In a preferred embodiment of a tapered root implant, the outer diameter of the implant as measured at the thread peaks remains relatively constant over the length of most of the implant. As the root diameter of the implant tapers down, the thread height increases such that the outer diameter of the implant as measured at the thread peaks remains relatively constant.

The present invention has at least one of a pair of implants having at least one side adapted to receive within the over-all circumference of the outer diameter of the implant the side of a second implant. In a preferred embodiment, the receiving implant has both leading and trailing support walls, and while preferable, but not requisite, these walls may provide structural support and nevertheless be highly perforated to allow for vascular access and the growth of bone through the implant. In a preferred embodiment of a second implant to be received within the first implant, the leading end support structure further comprises a cap, which cap need not, but may be threaded, and which cap need not be, but preferably is perforated.

In a preferred embodiment of the present invention, the trailing ends of the implants are rotationally asymmetrical about the mid-longitudinal axis such that they may be inserted in nested fashion and in proper rotational alignment relative to each other and to the vertebral bodies, with the result that the implants will have a length along the lateral aspect from leading to trailing end less than the length along the medial wall from leading end to trailing end. Preferably, the implants of the present invention are structurally adapted, such that when properly inserted, the length of the lateral side wall as measured from the leading end to the trailing end is of a lesser length than the length of the implant along its mid-longitudinal axis so as to prevent the protrusion of the lateral side wall and trailing end junction beyond the circumferentially curved profile of the vertebral bodies.

While the present invention does not require it, in a preferred embodiment the implants are adapted to receive through their trailing ends opposed bone screws and to transmit at least threaded portions of those screws through the opposite vertebrae engaging arcuate portions so as to allow those bone screws to engage at least one each into each of the vertebral bodies adjacent a disc space into which the implant are implanted.

Each of the embodiments of the implants of the present invention may also include one or more of anatomically contoured trailing ends, tapered minor diameters, opposed bone engaging screws, and locks for locking the opposed bone engaging screws into place. In a preferred embodiment, the implants of the present invention are configured to receive bone screw locks to lock the opposed bone screws to the implants. The bone screws are preferably lag screws and the locks, while preventing the backing out of the lag screws from the implant, may either be rigidly fixed or allow for continuing angular motion of the lag screws relative to the implants.

The present invention also is directed to an improved method for inserting such implants.

The accompanying drawings, which are incorporated in and constitute a part of this specification, are by way of example only and not limitation, and illustrate several embodiments of the invention, which together with the description, serve to explain the principles of the invention.

DETAILED DESCRIPTION OF THE DRAWINGS

The following description is intended to be representative only and not limiting and many variations can be anticipated according to these teachings, which are included within the scope of the present invention. Reference will now be made in detail to the preferred embodiments of this invention, examples of which are illustrated in the accompanying drawings.

Figure 1:
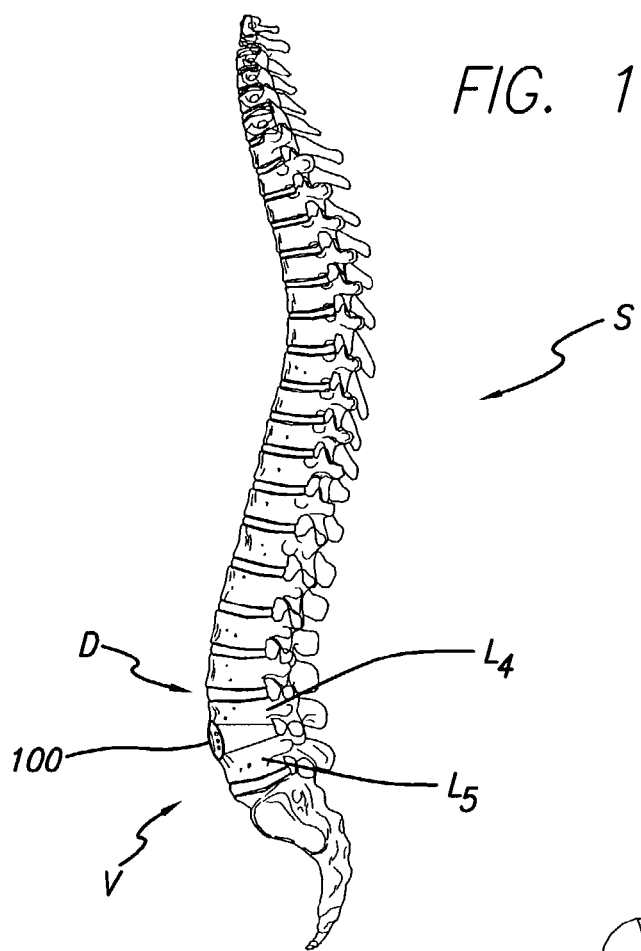
FIG. 1 is a side elevational view of the lateral aspect of the human spine with implants of an embodiment of the present invention implanted therein.

FIG. 1 is a side elevational view of the lateral aspect of a human lumbar spine S having vertebral bodies V and discs D interposed therebetween. The trailing end of an implant 100 can be seen located in the disc space between the fourth and fifth lumbar vertebrae $L_4$ and $L_5$ wherein disc space D has been distracted more anteriorly than posteriorly.

Figure 2:
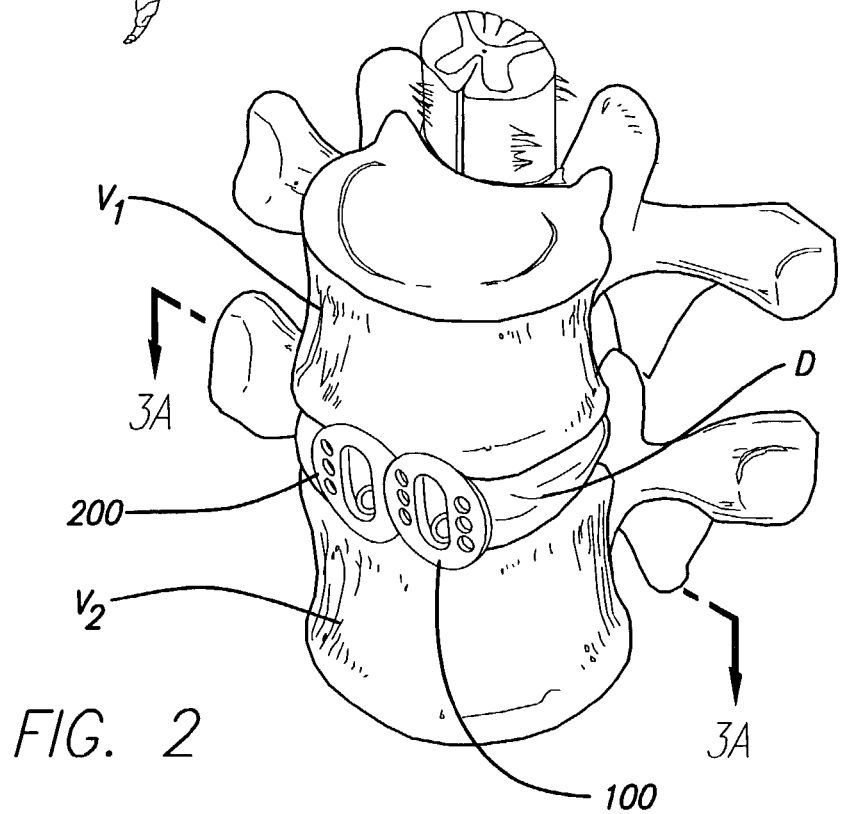
FIG. 2 is a front perspective view of two adjacent lumbar vertebrae and two implants of an embodiment of the present invention implanted across the disc space.

FIG. 2 is a front perspective view of adjacent vertebrae within a lumbar spine designated as $V_1$ and $V_2$. Interposed therebetween is a disc D, with paired implants 100 and 200 in nested side-by-side opposition inserted in the disc space. Implants 100 and 200 have heights greater than the height of the restored disc space into which they are implanted so as to expand the height of that disc space and to further penetrably engage into the bone of each of vertebral bodies $V_1$, $V_2$. In a preferred embodiment, the circumference of the trailing end of implant 100 preferably extends within the circumference of implant 200 when implants 100, 200 are in nested, longitudinal side-by-side placement.

As shown in FIGS. 3A, 4A, and 5-8, implants 100, 200 preferably each have a leading end 108, 208 for insertion first into the disc space; a trailing end 104, 204, opposite leading ends 108, 208, respectively; and a mid-longitudinal axis and length therebetween. Implants 100, 200 preferably each have upper and lower opposite arcuate portions 134, 134', and 234, 234' adapted for placement toward and at least in part within adjacent vertebral bodies $V_1$, $V_2$ and have a distance therebetween defining an implant height greater than the normal height of the disc space to be fused.

Preferably, opposite arcuate portions 134,134' and 234, 234' each have at least one opening 120, 220 communicating with one another for permitting the growth of bone from vertebral body to adjacent vertebral body through the implant. Preferably, at least a portion of a bone penetrating protrusion, such as thread 116, 216 is formed on the exterior of each of the opposite arcuate portions 134, 234, respectively, for penetrably engaging the adjacent vertebral bodies and to facilitate securing the implant into the spine by at least in part rotating the implant about its mid-longitudinal axis.

Figure 5:
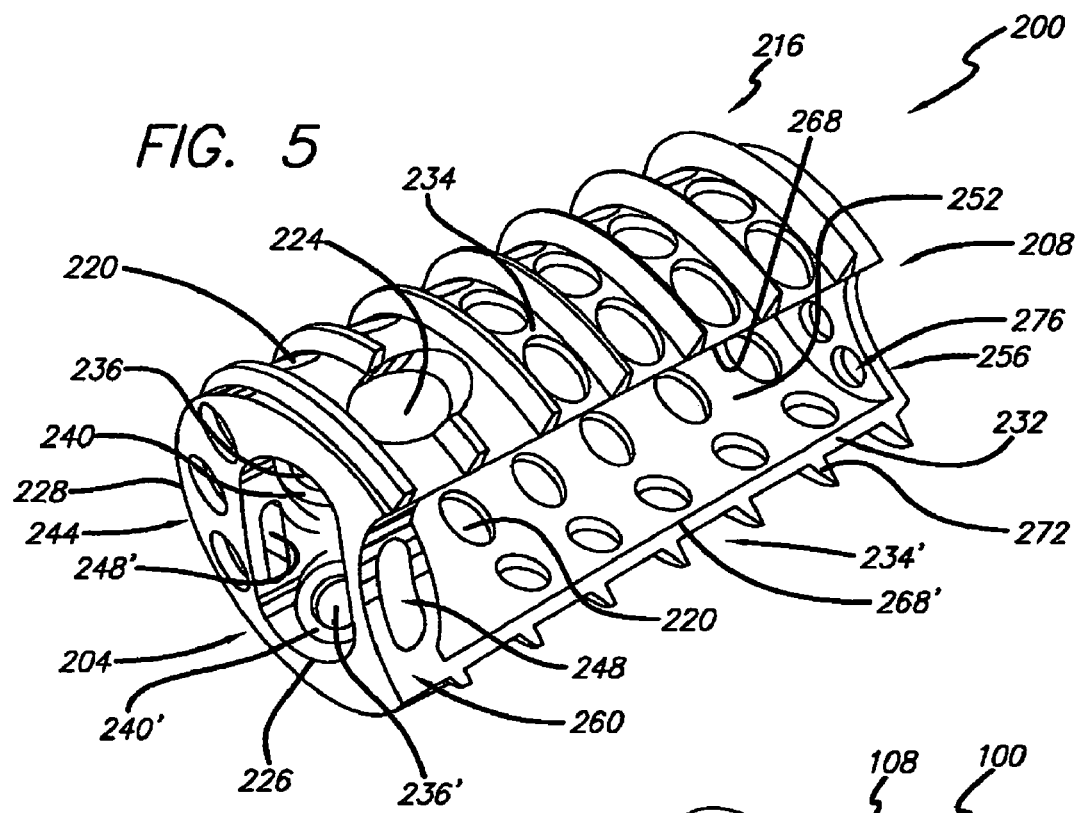
FIG. 5 is a side perspective view of an embodiment of an implant of the present invention.
Figure 6:
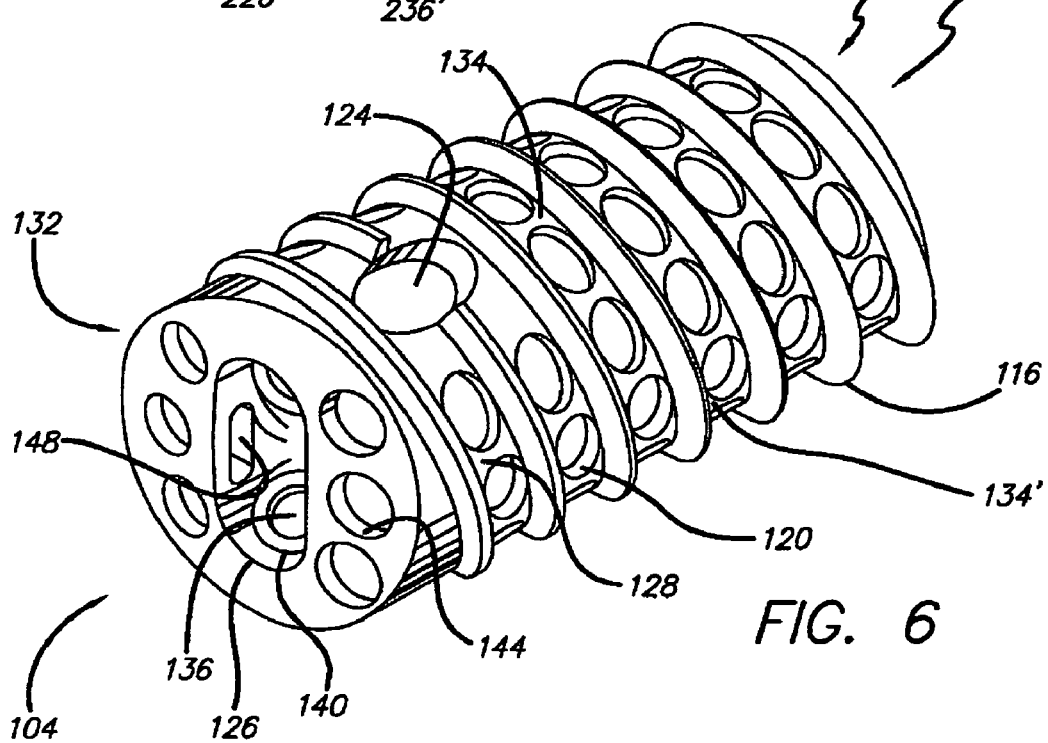
FIG. 6 is a side perspective view of another embodiment of an implant of the present invention.

FIGS. 5-8 show that in a preferred embodiment, implants 100, 200 have a body which is generally frusto-conical, increasing in diameter from leading end 108, 208 to trailing end 104, 204 and preferably has a helical thread 116, 216 about its circumference. Thread 116, 216 can have a generally constant outside diameter and can progress from a sharp pointed profile at the thread portion proximate leading end 108, 208 to a thicker and more squared profile toward trailing end 104, 204. Thread 116, 216 may be interrupted as shown in FIGS. 5 and 6. These specifics are shown by way of example only and not limitation. It is appreciated that implants 100, 200 may have any type of thread or threads useful for the intended purpose without departing from the present invention. Further, the implants of the present invention need not be frusto-conical as shown, and could be shaped much like a cylinder cut in half transversely through its mid-longitudinal axis with the upper and lower halves of the implant in angular relationship to each other.

In a preferred embodiment, the root diameter of the implants of the present invention tapers from its trailing end for placement anteriorly to its leading end for placement posterior within a disc space. This configuration is particularly desirable for providing for the proper lordotic relationship between the adjacent vertebral bodies, such that those vertebral bodies are distanced apart greater anteriorly than posteriorly. In a further preferred embodiment of these lordotic implants, the thread has a generally constant outside diameter such that in combination with the tapered root the actual thread height increases from the trailing end to the leading end progressively. At the leading end the thread may have a lesser height for facilitating the implant insertion without departing from this teaching.

Figure 7:
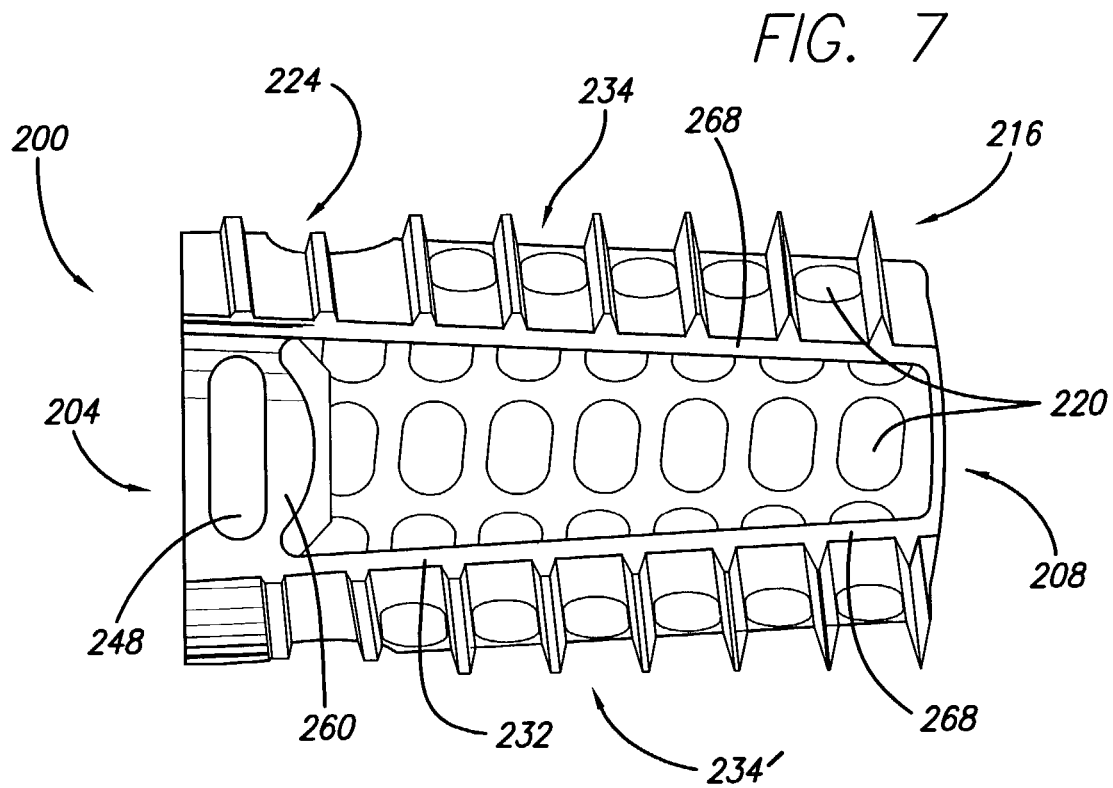
FIG. 7 is a side elevational view of the implant of FIG. 5.

FIGS. 5 and 7 show a preferred embodiment of implant 200. Lateral side wall 228 and medial side wall 232 have a distance therebetween defining an implant width transverse to the implant height. The width of implant 200 is less than its height along at least a portion of its length. Medial side wall 232 is preferably configured to be positioned in close proximity to at least implant 100 such that the combined width of implants 100, 200 is less than the combined height of those implants.

Implant 200 is similar to implant 100, but differs from implant 100 in that while the lateral sides 128 and 228 of implants 100 and 200, respectively, are the same and in this example convex, the medial side 232 of implant 200 has been relieved so as to allow for the convex medial side 132 of implant 100 to protrude therein. Alternatively, medial side of implant 200 can be relieved, in part absent, and/or concave.

Implant 200 also has at medial side 232 a convexity as shown by the contour of trailing support wall 260. In a preferred embodiment, leading support wall 256 may similarly be concave. And further a portion of the medial side wall 232 is absent so as to allow for the protrusion of implant 100 therein.

Figure 4A:
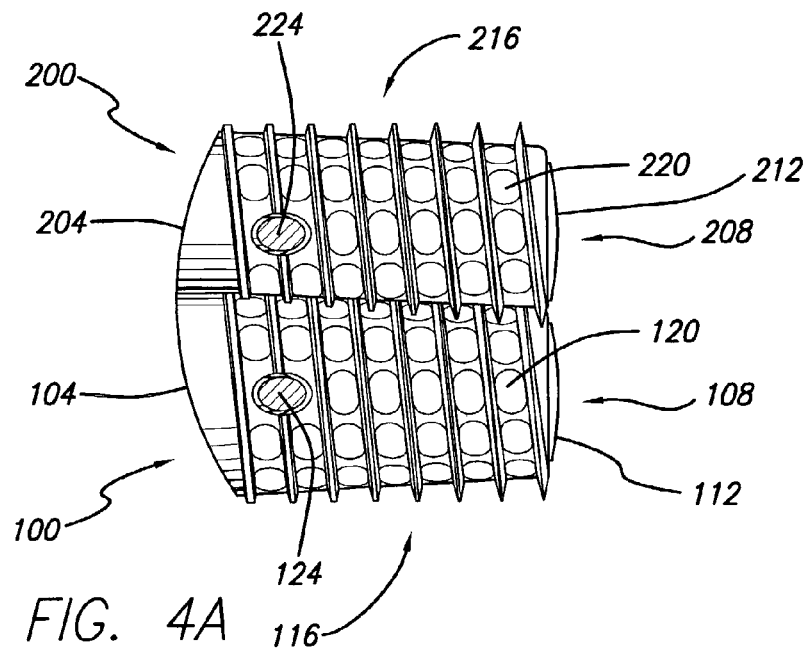
FIG. 4A is a top plan view of the implants of FIG. 3A.
Figure 4B:
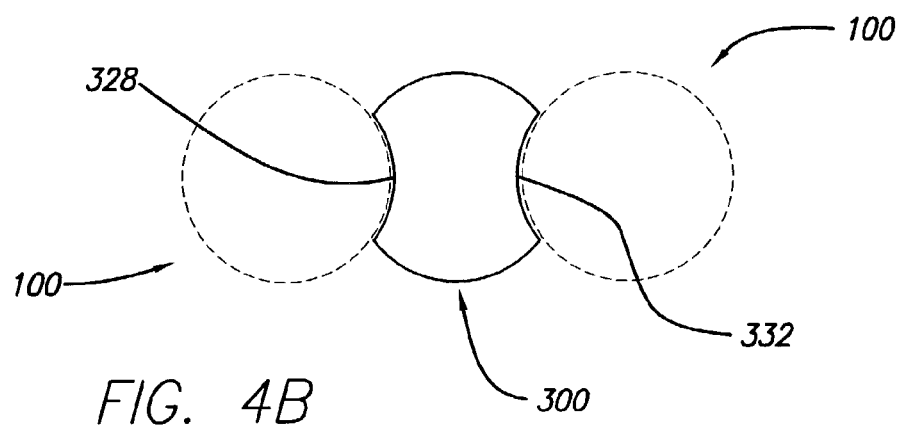
FIG. 4B is an end view of another embodiment of an implant of the present invention with two implants shown in hidden line.

As shown in FIG. 4B, in another embodiment of the present invention, an implant 300 may have a lateral side wall 328 and an opposite medial side wall 332. Both lateral side wall 328 and medial side wall 332 can be configured to be positioned in close proximity to two implants 100, one on each side of implant 300. The combined width of implant 300 and two implants 100 is less than the combined height of those implants.

Without departing from the scope of the present invention, the medial side of the implant need not be present as a single large opening 252 and could have a wall or support portion to it. In a preferred embodiment as shown, the large opening 252 allows for the easy packing of the implant with such osteogenic material as bone or a carrier containing bone morphogenetic protein or genetic material coding for the production of bone. A further advantage of the openness of this area is that it allows for further collateral vascularization to support bone growth from implant to implant. Again, while the present invention is not limited to a medial opening as shown, implant wall edge 268 can be continuous longitudinally to provide for strength in this critical area and if desired can be sharpened as can interrupted thread bases 272 so as to further facilitate the self-tapping nature of these implants.

In a preferred embodiment of the present invention, leading ends 108, 208 and trailing ends 104, 204 are also perforated. While leading end 208 could be more or less open, in a preferred embodiment there is a structural support portion 256 perforated by openings herein shown as 276. Trailing ends 104, 204 preferably have a plurality of openings 144, 244 therethrough to allow for vascular access into implants 100, 200 and the possibility of bone growth therethrough. Openings 144, 244 may also communicate with further openings such as 148, 148', 248, 248' to further increase the porosity of the trailing end of the implant. Implant 200 preferably is both hollow and highly perforated. Alternatively, the implants of the present invention can comprise a porous type of material such as a cancellously structured tantalum.

As can be appreciated from FIGS. 3A-4A, implant 100 is preferably structurally configured so as to cooperatively interdigitate into the maximum circumference of implant 200 along its length. When implant 100 is inserted within the circumference of implant 200 as shown in FIGS. 3A-4A, the combined width of implants 100 and 200 is substantially less than their combined heights, which heights in this case correspond to the maximum circumference of each of the implants which in this example is the same.

Figure 3A:
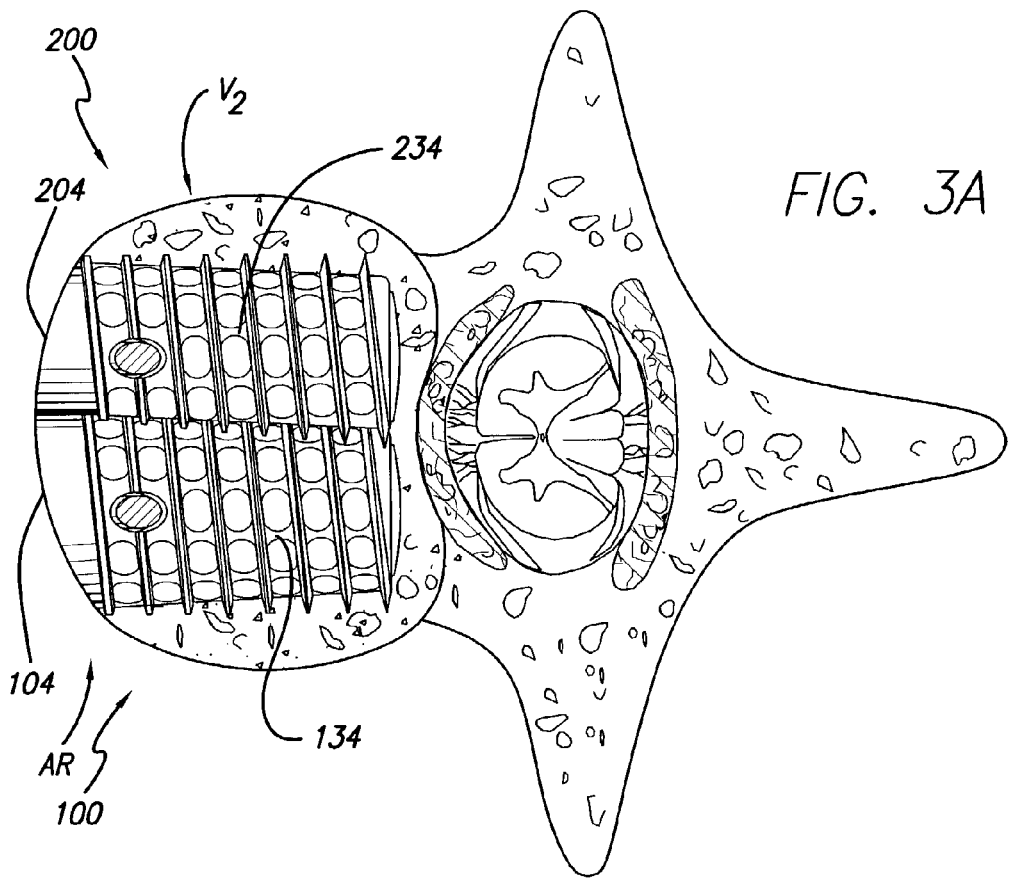
FIG. 3A is a top plan view of the implants of FIG. 2 and a cross section through a vertebra along line 3A-3A of FIG. 2.

While the implants of the present invention can have any of a variety of configurations at their trailing ends, trailing end 104 of implant 100, and trailing end 204 of implant 200 are preferably contoured to sit on the anterior rim AR of vertebral body $V_1$. As shown in FIG. 3A, trailing ends 104, 204 are asymmetrical about the mid-longitudinal axis of the implants 100, 200, respectively. In the final installed position of the implants, trailing ends 104, 204 preferably and generally conform to at least a portion of the anatomic curvature of the anterior rim AR of vertebral bodies $V_{1,2}$.

Figure 3B:
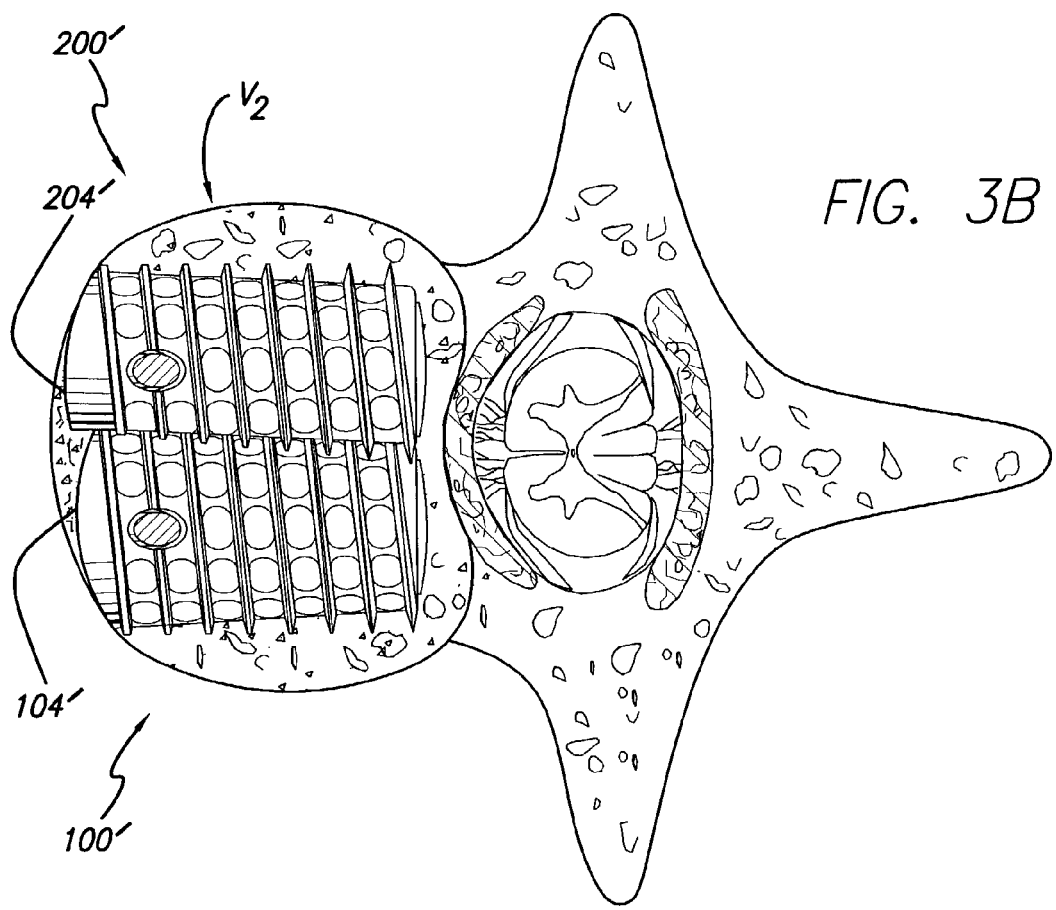
FIG. 3B is a top plan view of another embodiment of the implants of FIG. 3A and a cross section through a vertebra along line 3A-3A of FIG. 2.

As shown in FIG. 3B, alternatively, trailing end 104' of implant 100' may be symmetrical about the mid-longitudinal axis of implant 100' and trailing end 204' of implant 200' may be asymmetrical about the mid-longitudinal axis of implant 200'. Trailing ends 104', 204' are preferably contoured to sit on the anterior rim AR of vertebral body $V_2$.

Figure 3C:
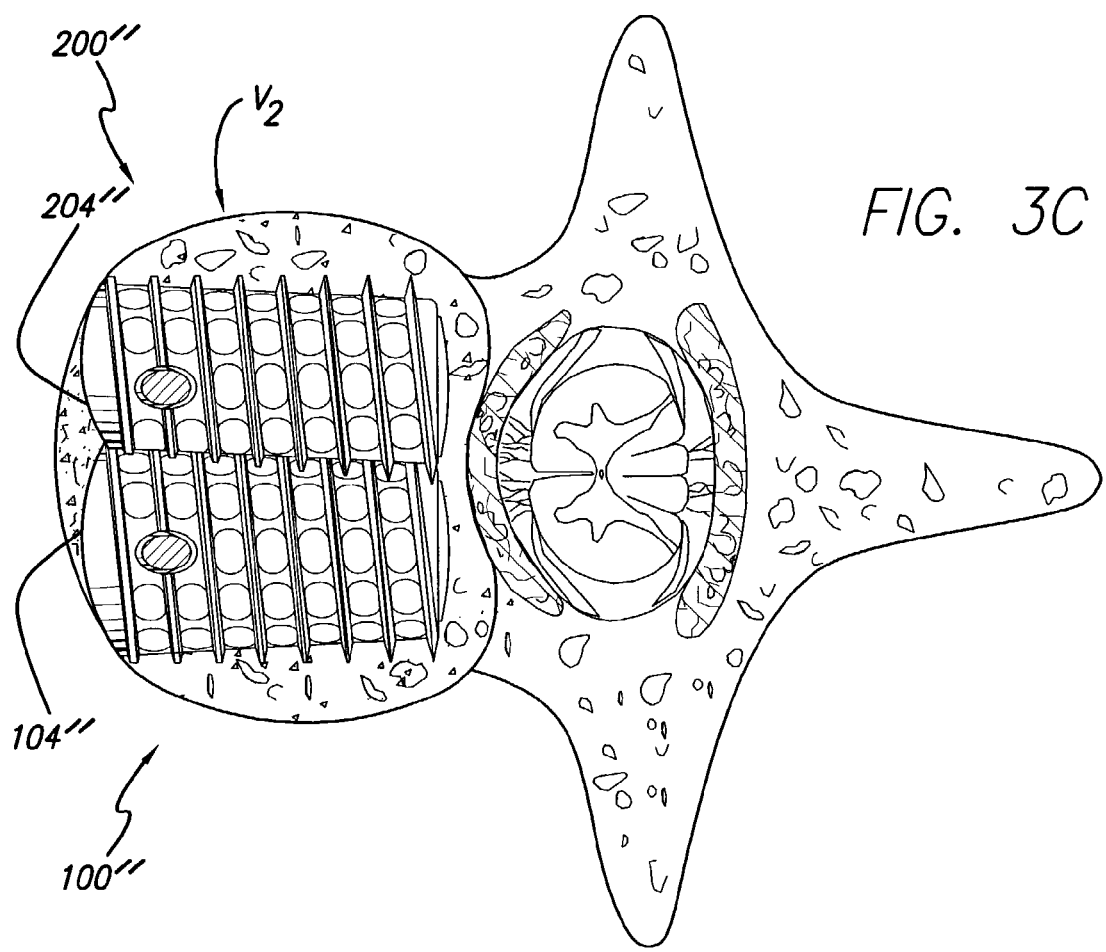
FIG. 3C is a top plan view of another embodiment of the implants of FIG. 3A and a cross section through a vertebra along line 3A-3A of FIG. 2.

As shown in FIG. 3C, alternatively, trailing end 104" of implant 100" and trailing end 204" may be symmetrical about the mid-longitudinal axes of implants 100", 200", respectively. Trailing ends 104", 204" are preferably contoured to sit on the anterior rim AR of vertebral body $V_2$.

Figure 8:
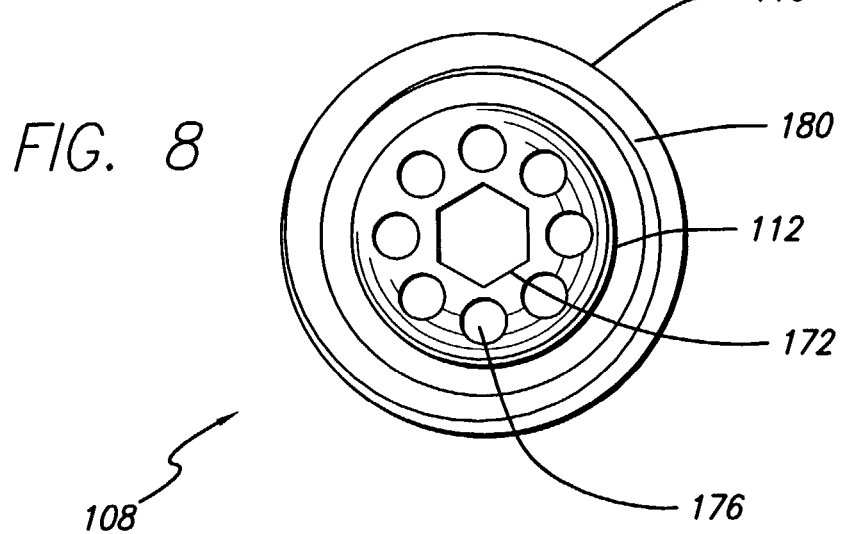
FIG. 8 is a leading end view of the implant of FIG. 6.

As best shown in FIG. 8, leading end 108 of implant 100 comprises an externally threaded cap 112 for threading into the internally threaded opening of leading end 108. Cap 112 is rotatable in either direction for opening and closing of implant 100 by cap 112 with hex opening 172 which can be manipulated with a hex driver. The specifics of cap 112, such as the bone holes 176, are shown by way of example only and not limitation. Cap 112 is useful for allowing for the compressive loading of the implant with osteogenic materials such as bone, demineralized bone matrix, carriers such as collagen or any other material useful as a carrier for the delivery of bone producing materials such as morphogenetic proteins, mineralizing proteins, or chemical compounds or genetic material coding for the production of bone. The cap itself may be more or less perforated and the opening themselves can be either larger or smaller, less or more, as desired to provide access to the interior of the implant, bone growth therethrough, and to the extent desired acts so as to contain the osteogenic material generally within the implant and from grossly expelling out of the leading end. The cap may be used as a structural member adding strength to the implant overall. Depending on the specific qualities desired, the cap can be made of any material appropriate for its purpose. Such materials would include various plastics, including polyethylene, and may include bioresorbable plastics as well. Such materials may include cortical bone, ceramic, or any surgical quality metal suitable for the intended purpose and including by way of example only and not limitation, surgical grade titanium and its alloys.

FIG. 4A is a top view of nested implants 100, 200 of FIG. 3A. As shown in FIG. 4A, the implants of an embodiment of the present invention are threaded on their exterior surface. While the embodiments shown have bone penetrating projections in the form of a helical thread, the present invention allows for a continuous thread, or an implant having thread portions such as would be useful for an implant to be inserted by linear advancement and then requiring an element of rotation, for example 90 degrees, to set the thread portions into the bone of the adjacent vertebral bodies.

As an alternative, the bone penetrating projecting segments need not be portions of a thread, but rather could be concentric projections generally, but not necessarily, oriented perpendicular to the long axis of the implants. For example, the projection may be a ridge or a fin adapted to penetrably engage the bone of the adjacent vertebral bodies.

As shown in FIG. 5, thread 116 of implant 100 may have a generally constant outer diameter. Inasmuch as the body of implant 100 is generally conical such that it tapers from the larger trailing end 104 to the smaller leading end 108, the height of thread 116 relative to body 102 increases from trailing end 104 to leading end 108. Thus, while the outer diameter of the threads remains generally constant, the height of the thread increases from trailing end 104 to leading end 108. This is similarly true for implant 200.

In a preferred embodiment of implant 100, 200 the start of the external thread about the perimeter of the implant is precisely indexed such that if the surgeon knows the depth of the bore created, he may select an implant of the desired length being less than or equal to the depth of the bore created and by starting the insertion of the implant in a preferred rotational alignment such as the desired final rotational alignment the implant when threaded in fully will come to rest such that trailing end 104, 204 will be correctly rotationally aligned so that screw receiving holes 236, 236' will be oriented correctly towards the adjacent vertebral bodies while the profile of trailing ends 104, 204 will correspond to the contour of the anterior vertebral body. A characteristic on the trailing end 104, 204 of each implant 100, 200 is adapted for indicating a rotational orientation of the openings 120, 220 in the upper and lower arcuate portions 134, 134', and 234, 234' relative to the adjacent vertebral bodies into which the implant 100, 200 is adapted to be inserted.

Trailing ends 104, 204 preferably include a characteristic adapted for indicating the rotational orientation of the openings in upper and lower arcuate portions 134,134', and 234, 234' relative to the adjacent vertebral bodies into which the implant is adapted to be inserted.

Preferably, the external thread of implant 100, 200 is indexed such that the ratio of the length of the implant relative to the pitch of the thread equals an integer. Such indexing allows the openings in upper and lower arcuate portions 134, 134', and 234, 234' to be oriented toward the adjacent vertebral bodies into which the implant is adapted to be inserted upon a predetermined number of complete rotations of the implant.

By way of example, for a bore measured to receive a 30 millimeter maximum length implant having a pitch of three millimeters as an example, the start of the thread at the implant leading end could be indexed such that the implant could be introduced rotationally oriented exactly as desired for the final positioning. Then, by making ten complete revolutions of three millimeters each the implant would assuredly come to rest with trailing wall 204 appropriately oriented and either be flush with the anterior vertebral cortices, or minimally counter-sunk to exactly the extent to which the surgeon caused the implant to enter the bore prior to initiating rotation. As previously mentioned, trailing end 204 of implant 200 could be rotationally asymmetrical, but nevertheless be symmetrical from side-to-side, such that each of the sides of the implant would be less protuberant posteriorly than a point along the mid-longitudinal axis such that the implant could be correctly inserted in increments of less than or equal to 180 degrees of rotation.

For example, the external thread of implant 100, 200 may be indexed such that the ratio of the length of the implant relative to the pitch of the thread equals a number that when divided by one of 0.25 and 0.5 equals an integer. Such indexing allows the openings in upper and lower arcuate portions 134, 134', and 234, 234' to be oriented toward the adjacent vertebral bodies into which the implant is adapted to be inserted upon a predetermined number of quarter and a half rotations of the implant.

While a preferred embodiment of the present invention is directed to a tapered root implant having a constant outer diameter thread, the present invention is not so limited. The present invention also would include implants having bodies that are more or less cylindrical. The present invention also would include other thread designs including a thread having a constant height relative to the body and with or without a constant outer diameter depending on the shape of the body.

As shown in FIG. 4A, extending through both upper and lower surfaces 134, 234 and located approximate trailing ends 104, 204 of implants 100, 200 are openings 124, 124', and 224, 224' respectively, for transmitting the threaded shafts of bone screws for engaging the adjacent vertebral bodies. While not so limited, a preferred embodiment of the present invention is adapted to receive a cancellous lag screw, having a head portion incapable of passing out of the implant so as to be contained therein. It is further preferred that the implant of the present invention are adapted to receive a lock for locking the opposite vertebrae engaging bone screws to the implants. Still further preferred is that the implants of the present invention are adapted to receive the lag screws and screw locks so as to allow the locks to function to prevent the backing out of the screws while, nevertheless allowing for some angular motion of the screws relative to the implants.

Figure 9:
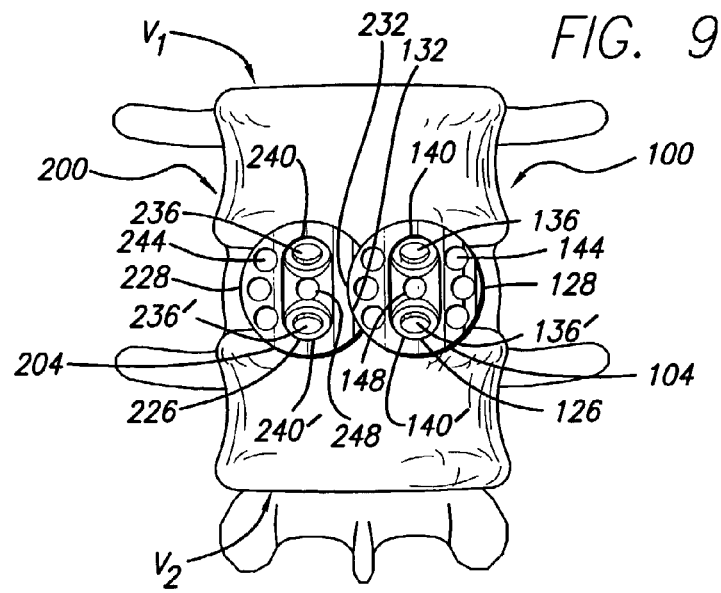
FIG. 9 is a front elevational view of two adjacent vertebrae in a lumbar spine with the implants of one embodiment of the present invention implanted across the disc space therebetween.

FIG. 9 shows a front view of an embodiment of the present invention with implants 100, 200 properly implanted across the disc space between adjacent vertebral bodies $V_1$ and $V_2$. Openings 144, 244 of implants 100, 200, respectively, allow for vascular access through trailing ends 104, 204 of implants 100, 200 and for bone growth therethrough. Trailing ends 104, 204 have common openings 126, 226 and situated essentially therein, are threaded openings 148, 248 for receiving an implant driver. The implant driver has a distal end for a complimentary fit within common openings 126, 226 and therethrough a rotatable threaded member for threading into openings 148, 248, respectively. Openings 126, 226 also are adapted to receive a screw device to link the implant to other implants, to a staple, or to receive a locking screw to lock bone engaging screws to the implant as disclosed in Michelson U.S. patent application Ser. No. 08/926,334 incorporated herein by reference. Common opening 126, 226 also may have therein opposed and divergently angled openings 136, 236 and 136', 236' adapted to receive opposed vertebral bone engaging screws. Bone screw receiving openings 136, 236 and 136', 236' preferably may have circumferentially around them retaining seats 140, 240 and 140', 240' adapted to receive and to block the passage of the heads of screws to be inserted therethrough. Retaining seats 140, 240, and 140', 240' may also be flanged.

As shown in the preferred embodiment of the present invention, trailing ends 104 and 204 of implants 100 and 200, respectively, preferably are rotationally asymmetrical about the longitudinal axes of the implants such that the designated medial side of each of the implants has a length greater than the lateral sides of the same implants. Trailing ends 104, 204 preferably are structured to have a lesser length along their lateral sides than through the mid-longitudinal axis and are preferably contoured so as to sit on the anterior rims of the vertebral bodies without protruding dangerously therefrom as set forth in pending Michelson application Ser. No. 09/263, 266 incorporated herein by reference. In another embodiment of the present invention, the trailing ends of the implants can have a maximum length along the mid-longitudinal axis greater than the length along either of the medial and lateral sidewalls so that the bone screw receiving holes can be oriented towards the adjacent vertebral bodies in half rotation increments rather than requiring a full rotation. While for implant 100 this would require no other modification than as described for the trailing end, in regard to implant 200 each of the lateral and medial side walls would have to be relieved, as shown in FIG. 4B for example, to allow for the receipt of the perimeter of implant 100 within the maximum perimeter of implant 200.

FIGS. 10-14 show a series of steps useful for discussing a method of use of the present invention implants. Methods for inserting spinal implants are discussed in part in issued and pending patent applications to Michelson U.S. Pat. Nos. 5,593,409, 5,741,253, 5,484,437, 08/396,414, and 08/480, 904, incorporated by reference herein. The disc space to be used is preferably, but not necessarily, distracted to optimal height and the vertebral bodies preferably, but not necessarily, properly aligned. A pair of overlapping bores are then formed across the disc space with a bone removal device such as a drill having a diameter greater than the height of a distracted disc space such that arc-shaped portions of bone are removed from each of the vertebral bodies adjacent the disc space to be fused. The overlapping bores are generally oriented from anterior to posterior and preferably stop short of the spinal canal.

Figure 10:
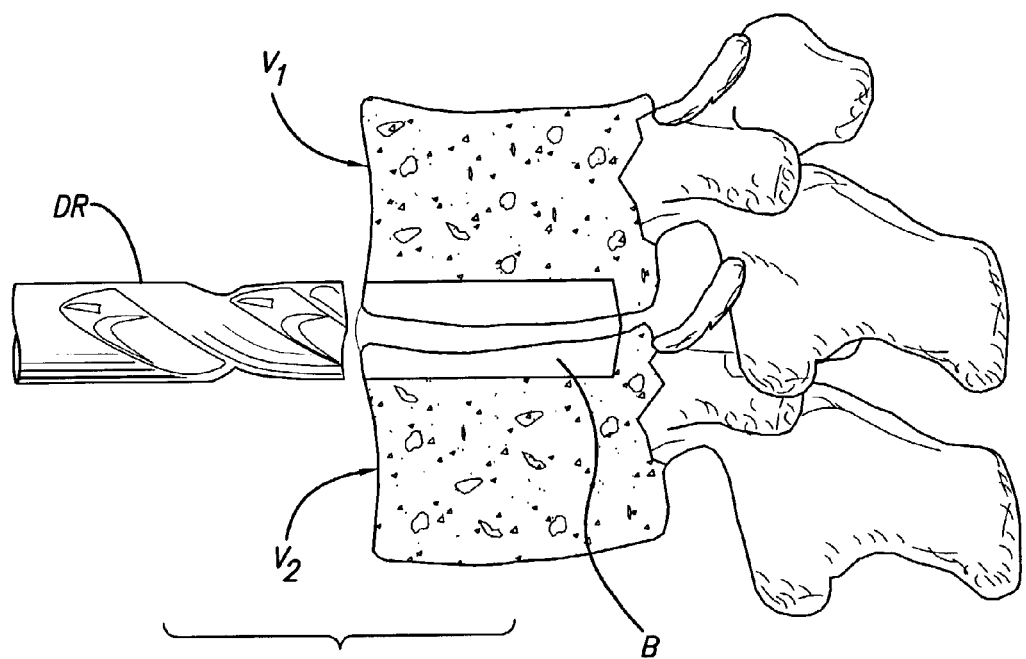
FIG. 10 is a cross sectional side elevational view of the lateral aspect of two adjacent lumbar vertebrae illustrating the bore created by a drill.

A bone removal device such as a drill or mill that may be conical can be utilized to complement the tapered configuration of the implant body. As shown in FIG. 10, however, in a preferred method a generally cylindrical drill DR or end mill is utilized to create a generally cylindrical bore for receiving the implants. When a pair of generally cylindrical overlapping bores, preferably but not necessarily, having a diameter generally corresponding to that of the root diameter of the implant proximate the leading end are formed as per FIG. 3A, the implants will come to be positioned such that the combined width of the implants at their leading ends will be less than the combined width of implants at their trailing end. That is, the implants will be angled in towards each other from anterior to posterior. This has the further benefit of swinging the junction of the lateral side walls and trailing ends further inward and away from escaping the anterior vertebral cortex, thereby avoiding protrusion of the lateral side wall to trailing end junctions and allowing for the installation of larger and longer implants than might otherwise be possible.

As has been taught by Michelson in the above identified applications and patents incorporated by reference herein, the disc space may be distracted in any number of ways and held distracted during the bore formation portion of the procedure. Some of the preferred ways include the use of long distractors, short distractors, and extended outer sleeves having distractor members for placement within the disc space and between the adjacent vertebral bodies as described by Michelson in the above described applications and patents incorporated by reference herein. Other distractors such as those which attach to the vertebral bodies as by pins or screws might also be useful for the present intended purpose.

While surgery may be performed through a single bore first, in a preferred embodiment both bores are created in overlapping fashion prior to the insertion of the first implant which in this example is implant 200. Implant 200 is affixed to an implant driver which driver preferably engages the implant at trailing wall 204 by interdigitating with implant 200 and further binding to implant 200 by a thread such that it is possible both to rotate implant 200 in either direction and to push or pull simultaneously. While that may be achieved by having a driver which interdigitates with any of the openings into or through rear wall 204 and having a rotatable portion for threading into threaded opening 248 the present invention is not so limited and may include any driver useful for the intended purpose.

After implant 200 is fully seated with medial side wall 228 oriented immediately toward the disc space, a complementary implant 100 is inserted by allowing it to rotate within the maximum circumference of implant 200. Pre-tapping the bores formed across the disc space prior to the insertion of the implants does not deviate from the present teaching. In a preferred embodiment, pre-tapping is not required as certain preferred embodiments of the present implants are tapered from their trailing to their leading ends and the leading ends have particularly significant thread heights making their ability to thread themselves into the bone particularly effective.

Figure 11:
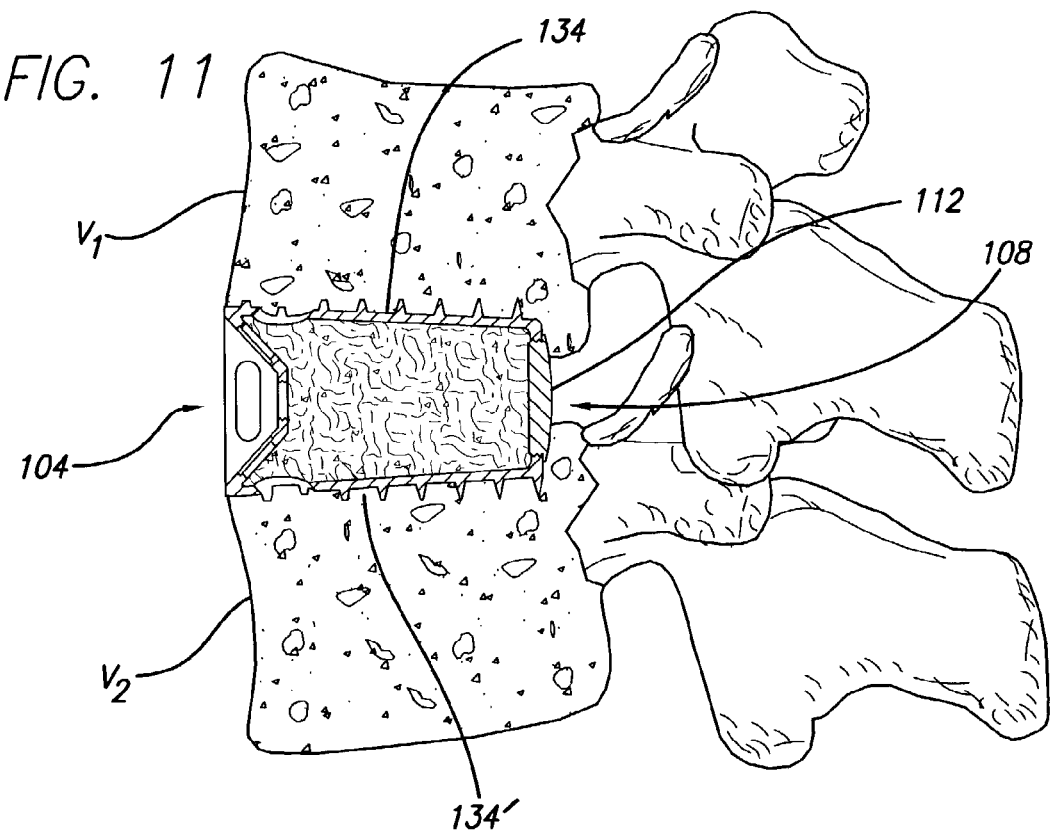
FIG. 11 is a cross sectional side elevational view of the lateral aspect of two adjacent vertebrae and an embodiment of an implant of the present invention inserted therebetween.
Figure 12:
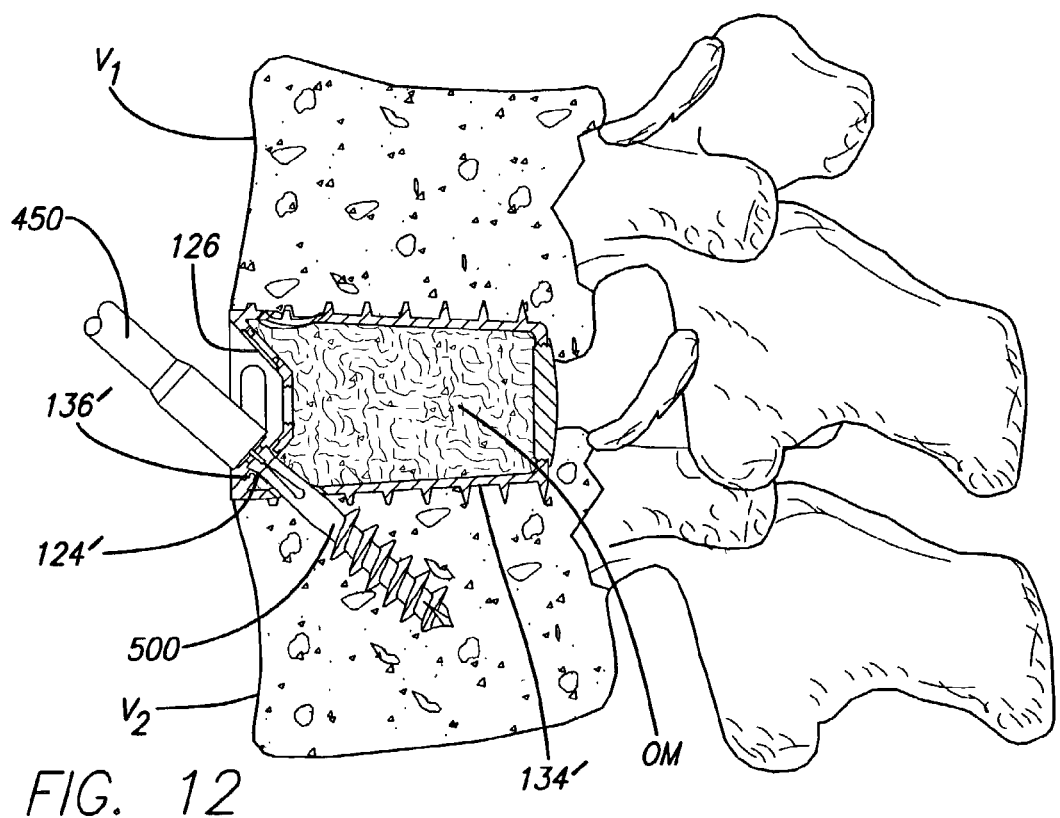
FIG. 12 is a cross sectional side elevational view of the adjacent vertebrae and implant of FIG. 11 with a screw driver and a bone engaging screw being installed.

FIGS. 11-14, show openings at the trailing end of the implant for receiving opposed screws that may be oriented from the implant into each of the adjacent vertebral bodies. These screws enter the implant through the trailing end and the threaded shafts of the screws pass through openings in the opposite upper and lower vertebral body engaging surfaces of the implants. Shown in FIG. 11 is a cut away through implant 100 of FIG. 9. This is a cross section through the mid-longitudinal axis of implant 100 and the adjacent vertebral bodies. FIG. 12 shows a screw driver 450 driving a bone screw 500 through common opening 126, bone screw receiving hole 136' and out opening 124' through lower vertebrae engaging surface 134' into adjacent vertebral body $V_2$. The present invention includes the use of any bone screws for this described purpose. In preferred embodiments, structure is provided to block the bone screws from disengaging from the implant or backing out. The screws may be rigidly locked to the implant or may be prevented from backing out in a manner that still allows for some relative motion between the screws and the implant. The latter may be beneficial for anticipating and allowing for some settling of the vertebral bodies towards the disc space.

Figure 13:
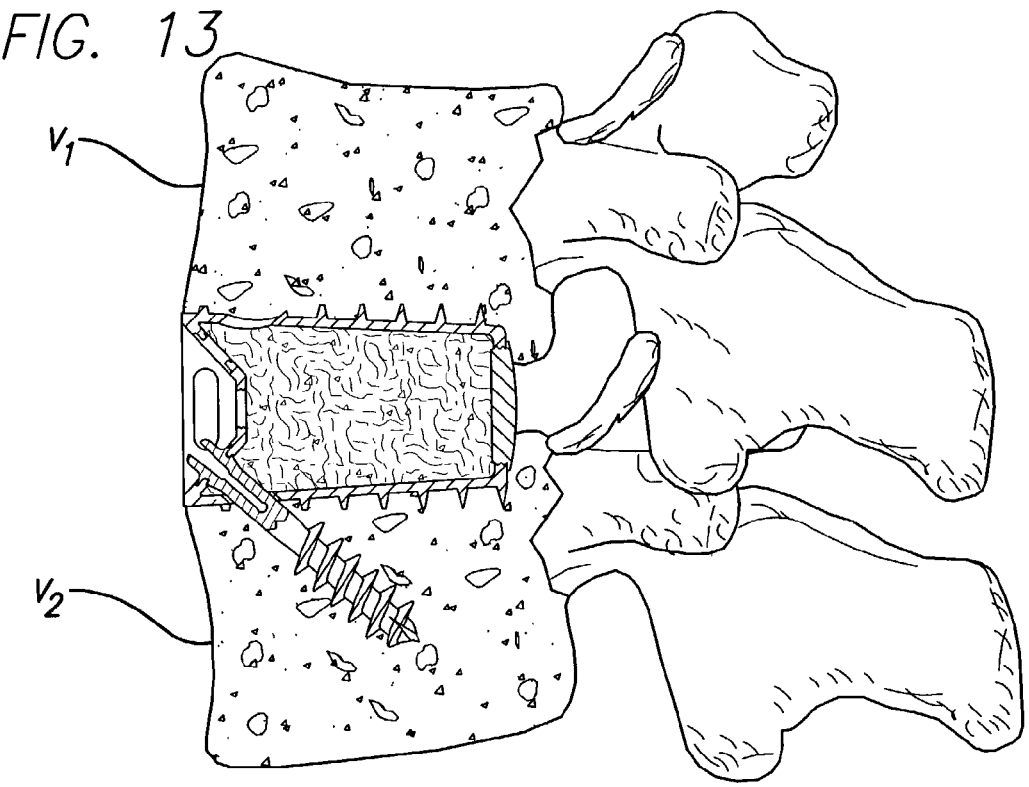
FIG. 13 is a side elevational cross sectional view of the adjacent vertebrae and the implant of FIG. 11 with a bone engaging screw in the installed position.
Figure 14:
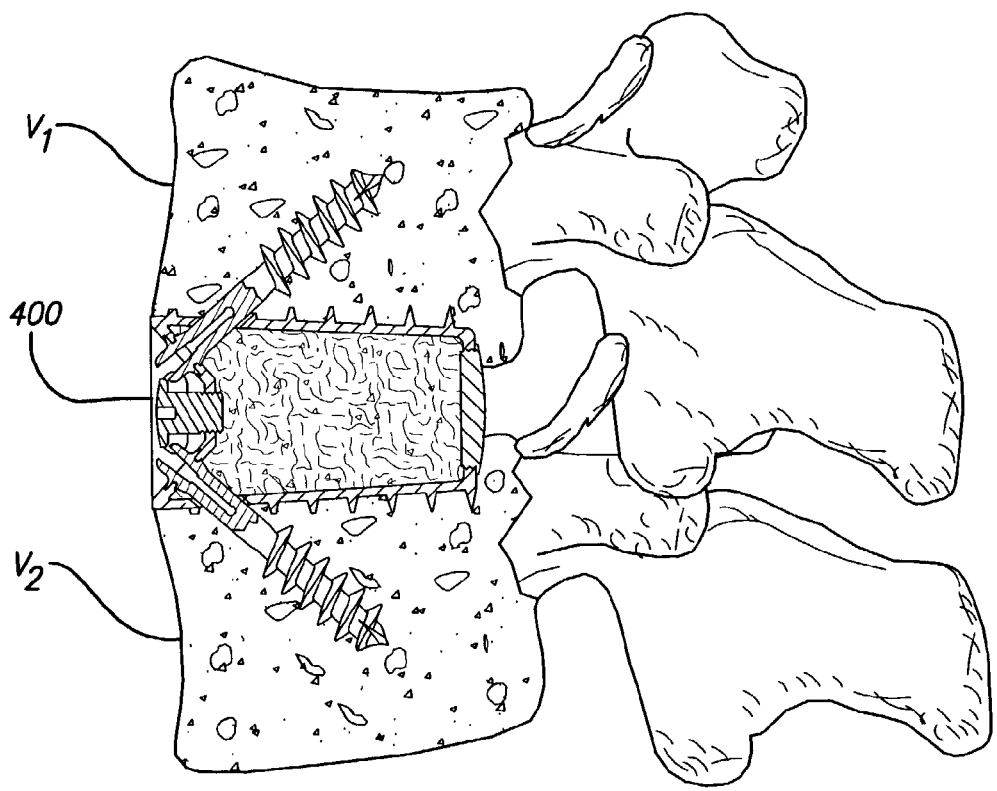
FIG. 14 is a side elevational cross sectional view of the adjacent vertebrae and implant of FIG. 11 with two bone engaging screws in the installed positioned.

In use, as shown in FIG. 12, the driver 450 is assembled to the screw 500 thereby compressing the head portion of the screw. The screw is then introduced through the trailing end of the implant and directed into the body of one of the adjacent vertebrae passing out of an opening adapted for that purpose in one of the opposite vertebrae engaging surfaces of the implant. The head of the screw 500 is too large to pass through the opening in the implant, and yet is free to spin against the implant itself making it possible to lag the screw, or that is to draw the body of the vertebra to the implant and to generate compressive load between the implant and the vertebral body. As shown in FIG. 13, when the screw has been fully seated and the driver removed, the head of the screw is free to reexpand, thereby locking it to the implant. As mentioned, the present invention includes the use of any opposed vertebrae engaging bone screws, such that at least one each of said screws binds the implant to each of the adjacent vertebral bodies. In a preferred embodiment, the screws are prevented from backing out of the implant. Screws may be locked directly to the implant such that they are rigidly attached thereto, or may be capable of some movement relative to the implant so as to allow for variation in screw positioning and/or settling of the vertebrae, and yet be prevented from backing out.

While the present invention is shown in a preferred embodiment as both highly perforate and substantially hollow, the implant could comprise a generally porous or cancellous material allowing for the growth of bone in continuity from vertebrae to vertebrae through the implant. The present invention implants can comprise of any material that is biocompatible and structurally suitable for construction of these interbody spinal fusion implants and consistent with the growth of bone from vertebral body to vertebral body through the implants. To that end, materials which would be satisfactory might include implant quality metals such as surgical quality titanium and its alloys, cobalt chrome or other metals useful for this purpose, cortical bone and in particular human cortical bone such as that which might be obtained from one of the tubular long bones of a human body, ceramics, plastics and composite materials including those incorporating carbon fibre; and such implants may further comprise, contain, be treated with or coated with osteogenic materials other than bone for the purpose of achieving spinal fusion. Such materials would include but not be limited to bone morphogenetic protein, ossification inducing proteins, and genes coding for the production of bone. Further, the implants may include at least in part or wholly materials bioabsorbable by the human body, which by way of example only may include plastics selected from the lactide, lactone family, polylactide, polylactone family, glycolic acid derivatives and so forth.

The implants of the present invention may be coated with, comprised of, be used in combination with, or have a hollow for containing bone growth promoting materials, including but not limited to, bone morphogenetic proteins, hydroxyapatite, and genes coding for the production of bone. The implants of the present invention can be formed of a material that intrinsically participates in the growth of bone from one of adjacent vertebral bodies V to the other of adjacent vertebral bodies V.

While the specific preferred embodiments the implants of the present invention have been described, again the present invention is not so limited. The present invention includes any interbody spinal fusion implants embodying the present teachings including implants having opposite surfaces with a thread, portion of a thread, or generally concentric fins used to penetrably engage the substance of the vertebral bodies when the implants are rotated about their longitudinal axes approximately 90 degrees or more.

The implants of the present invention are preferably hollow with a plurality of openings through the various surfaces of the implant in communication with the implant hollow. The present invention includes either fewer, or more openings so long as each of the opposite vertebrae engaging surfaces of the implant have at least one opening in communication with the other so as to allow for the growth of bone in continuity from vertebral body to adjacent vertebral body through the implant.

There is disclosed in the above description and the drawings implants, which fully and effectively accomplish the objectives of this invention. However, it will be apparent that variations and modifications of the disclosed embodiments may be made without departing from the principles of the invention or the scope of the appended claims.

What is claimed is:

1. An interbody spinal fusion implant for surgical implantation at least in part within a disc space between two adjacent vertebral bodies in a segment of a human spine, said implant comprising:

opposed upper and lower arcuate portions for contacting each of the adjacent vertebral bodies when positioned therein, each of said upper and lower arcuate portions having at least one opening adapted to communicate with one of the adjacent vertebral bodies, said openings of said upper and lower portions being in communication with one another and adapted for permitting for the growth of bone from adjacent vertebral body to adjacent vertebral body through said implant;

at least a portion of a helical thread formed on the exterior of each of said opposed arcuate portions for penetrably engaging the adjacent vertebral bodies and to facilitate securing said implant into the spine by at least in part rotating said implant about a longitudinal axis of said implant, said thread having a pitch;

an insertion end for entry into the spine, a trailing end opposite said insertion end, and a length therebetween, said trailing end having a perimeter with opposed sides, said trailing end having an exterior surface spaced apart from said thread, said exterior surface extending from one of said opposed sides to another of said opposed sides of said perimeter; and a characteristic on at least said exterior surface of said trailing end of said implant, said characteristic being spaced apart from said thread, said characteristic being adapted to indicate a rotational orientation of said upper and lower arcuate portions relative to the adjacent vertebral bodies into which said implant is adapted to be inserted, the length and pitch of said implant having a ratio relative to one another such that the length of said implant when divided by the pitch of said thread equals an integer, said characteristic being configured to indicate an initial insertion orientation of said implant, said thread having a starting point proximate said insertion end, said starting point of said thread being indexed such that insertion of said implant in said initial insertion orientation positions said upper and lower arcuate portions toward the adjacent vertebral bodies upon a predetermined number of complete rotations of said implant.

2. The implant of claim 1, further comprising a medial side that includes an opening along a majority of the length of said implant.

3. The implant of claim 1, further comprising a lateral side that is open along at least a portion of the length of said implant.

4. The implant of claim 1, further comprising a medial side that is at least in part concave along the length of said implant.

5. The implant of claim 1, wherein said perimeter of said trailing end proximate a medial side of said implant being configured to receive at least a portion of a perimeter of a trailing end of a second implant when the second implant is placed in close proximity to said implant.

6. The implant of claim 1, wherein said implant has an outer diameter having a circumference and a medial side adapted to receive at least a portion of the circumference of an outer diameter of a second implant.

7. The implant of claim 1, further comprising a medial side including an aperture for loading bone growth promoting material into a hollow interior of said implant.

8. The implant of claim 7, wherein said bone growth promoting material is compressively loaded into said implant.

9. The implant of claim 1, wherein said trailing end is rotationally asymmetrical along its mid-longitudinal axis.

10. The implant of claim 1, wherein said trailing end is anatomically contoured to correspond to the natural contour of at least a portion of the anterior aspect of the vertebral bodies.

11. The implant of claim 1, wherein said trailing end is contoured to sit proximate to the anterior rim of the vertebral bodies and conforms thereto.

12. The implant of claim 1, wherein said implant has a lesser length along a lateral side than along its mid-longitudinal axis.

13. The implant of claim 1, including opposed and divergently angled bone screw receiving openings extending from said trailing end and through said upper and lower arcuate portions adapted to receive opposed vertebral bone engaging screws, said implant being configured so that said bone screw receiving openings are adapted to be oriented towards the adjacent vertebral bodies in half rotation increments of said implant.

14. The implant of claim 1, wherein said trailing end is configured to cooperatively engage an implant driver.

15. The implant of claim 1, wherein said thread has peaks, said peaks being relatively constant along the length of said implant so that an outer diameter of said implant is generally constant.

16. The implant of claim 1, wherein said thread has a substantially constant height as measured from said upper and lower arcuate portions over a substantial portion of the length of said implant.

17. The implant of claim 1, wherein said thread is interrupted.

18. The implant of claim 1, wherein said thread is configured for linear advancement of said implant and requires an element of rotation to set said thread into the bone of the adjacent vertebral bodies.

19. The implant of claim 18, wherein said element of rotation is approximately 90 degrees.

20. The implant of claim 1, wherein said thread has a sharp pointed profile at said insertion end and progresses to a thicker and more squared profile at said trailing end.

21. The implant of claim 1, wherein said thread is a projection generally oriented perpendicular to the mid-longitudinal axis.

22. The implant of claim 1, wherein said thread forms a single helix.

23. The implant of claim 1, wherein said thread is one of a fin and a ridge.

24. The implant of claim 1, further comprising a hollow interior adapted to receive fusion-promoting substances.

25. The implant of claim 24, wherein at least one of said insertion and trailing ends is open to allow access to said hollow interior.

26. The implant of claim 1, wherein said upper and lower arcuate portions form at least a portion of a cylinder along the length of said implant.

27. The implant of claim 1, wherein said upper and lower arcuate portions form a generally frusto-conical shape.

28. The implant of claim 1, wherein said implant is tapered along a substantial portion of its length.

29. The implant of claim 1, wherein at least one of said upper and lower arcuate portions has a screw hole adapted to transmit a screw therethrough and into one of the vertebral bodies, said trailing end adapted to receive a screw therethrough and passing through a hollow interior of said implant and through said screw hole and into one of the adjacent vertebral bodies.

30. The implant of claim 29, further comprising at least one screw adapted to pass from said hollow interior of said implant through said screw hole and into the adjacent vertebral body to anchor said implant to the adjacent vertebral body.

31. The implant of claim 1, wherein said trailing end is adapted to receive opposed bone screws and to transmit at least a portion of the screws through said upper and lower arcuate portions so as to engage at least one each into each of the vertebral bodies adjacent the disc space.

32. The implant of claim 1, wherein said trailing end includes opposed and divergently angled openings extending from said trailing end and through said upper and lower arcuate portions adapted to receive opposed vertebral bone engaging screws.

33. The implant of claim 29, wherein said trailing end includes retaining seats circumferentially around said screw hole adapted to receive and to block the passage of at least a portion of the screw to be inserted therethrough.

34. The implant of claim 29, wherein said trailing end is configured to cooperatively engage a lock for locking opposed bone screws to said implant.

35. The implant of claim 29, further including a lock for preventing backing out of bone screws from said implant.

36. The implant of claim 35, wherein the bone screws are lag screws and said lock allows for angular motion of the lag screws relative to said implant.

37. The implant of claim 36, wherein said lock is insertable into said implant.

38. The implant of claim 29, in combination with a bone screw.

39. The implant of claim 38, in combination with a lock for locking said bone screw.

40. The implant of claim 1, further comprising a cap for closing at least one of said ends of said implant, said cap having an exterior surface and an interior surface.

41. The implant of claim 40, wherein said interior surface of said cap has spaced slots about its circumference to facilitate a snap fit of said cap into said implant.

42. The implant of claim 40, wherein said cap includes a threaded portion for threadably engaging said insertion end of said implant.

43. The implant of claim 40, wherein said cap is perforated.

44. The implant of claim 1, wherein said implant comprises bone.

45. The implant of claim 44, wherein said bone includes cortical bone.

46. The implant of claim 1, wherein said implant comprises bone growth promoting material.

47. The implant of claim 46, wherein said bone growth promoting material is selected from one of bone morphogenetic protein, hydroxyapatite, and genes coding for the production of bone.

48. The implant of claim 1, wherein said implant is treated with a bone growth promoting substance.

49. The implant of claim 1, wherein said implant is a source of osteogenesis.

50. The implant of claim 1, wherein said implant is at least in part bioabsorbable.

51. The implant of claim 1, wherein said implant comprises a plastic material.

52. The implant of claim 1, wherein said implant comprises a ceramic material.

53. The implant of claim 1, wherein said implant is formed of a porous material.

54. The implant of claim 1, wherein said implant is formed of a material that intrinsically participates in the growth of bane from adjacent vertebral body to adjacent vertebral body through said implant.

55. The implant of claim 1, wherein said at least one opening is adapted to retain fusion-promoting materials.

56. The implant of claim 1, wherein at least a portion of said implant is treated to promote bone ingrowth between said implant and said adjacent vertebral bodies.

57. The implant of claim 1, in combination with a chemical substance to inhibit scar formation.

58. The implant of claim 1, wherein said implant comprises cancellously structured tantalum.

59. The implant of claim 1, wherein said characteristic and said starting point of said thread are coordinated to indicate a distinctive initial rotational orientation and insertion position of said implant to orient said upper and lower arcuate portions toward the adjacent vertebral bodies after rotation of said implant to a final installed position.

60. An interbody spinal fusion implant for surgical implantation at least in part within a disc space between two adjacent vertebral bodies in a segment of a human spine, said implant comprising:

opposed upper and lower arcuate portions for contacting each of the adjacent vertebral bodies when positioned therein, each of said upper and lower arcuate portions having at least one opening adapted to communicate with one of the adjacent vertebral bodies, said openings of said upper and lower portions being in communication with one another and adapted for permitting for the growth of bone from adjacent vertebral body to adjacent vertebral body through said implant;

at least a portion of a helical thread formed on the exterior of each of said opposed arcuate portions for penetrably engaging the adjacent vertebral bodies and to facilitate securing said implant into the spine by at least in part rotating said implant about a longitudinal axis of said implant, said thread having a pitch;

an insertion end for entry into the spine, a trailing end opposite said insertion end, and a length therebetween, said trailing end having a perimeter with opposed sides, said trailing end having an exterior surface spaced apart from said thread, said exterior surface extending from one of said opposed sides to another of said opposed sides of said perimeter; and a characteristic on at least said exterior surface of said trailing end of said implant, said characteristic being spaced apart from said thread, said characteristic being adapted to indicate a rotational orientation of said upper and lower arcuate portions relative to the adjacent vertebral bodies into which said implant is adapted to be inserted, the length and pitch of said implant having a ratio relative to one another such that the length of said implant when divided by the pitch of said thread equals a number that when divided by one of 0.25 and 0.5 equals an integer, said characteristic being configured to indicate an initial insertion orientation of said implant, said thread having a starting point proximate said insertion end, said starting point of said thread being indexed such that insertion of said implant in said initial insertion orientation positions said upper and lower arcuate portions toward the adjacent vertebral bodies upon one of a predetermined number of a quarter and a half rotations of said implant.

61. The implant of claim 60, further comprising a medial side that includes an opening along a majority of the length of said implant.

62. The implant of claim 60, further comprising a lateral side that is open along at least a portion of the length of said implant.

63. The implant of claim 60, further comprising a medial side that is at least in part concave along the length of said implant.

64. The implant of claim 60, wherein said perimeter of said trailing end proximate a medial side of said implant being configured to receive at least a portion of a perimeter of a trailing end of a second implant when the second implant is placed in close proximity to said implant.

65. The implant of claim 60, wherein said implant has an outer diameter having a circumference and a medial side adapted to receive at least a portion of the circumference of an outer diameter of a second implant.

66. The implant of claim 60, further comprising a medial side including an aperture for loading bone growth promoting material into a hollow interior of said implant.

67. The implant of claim 66, wherein said bone growth promoting material is compressively loaded into said implant.

68. The implant of claim 60, wherein said trailing end is rotationally asymmetrical along its mid-longitudinal axis.

69. The implant of claim 60, wherein said trailing end is anatomically contoured to correspond to the natural contour of at least a portion of the anterior aspect of the vertebral bodies.

70. The implant of claim 60, wherein said trailing end is contoured to sit proximate to the anterior rim of the vertebral bodies and conforms thereto.

71. The implant of claim 60, wherein said implant has a lesser length along a lateral side than along its mid-longitudinal axis.

72. The implant of claim 60, including opposed and divergently angled openings extending from said trailing end and through said upper and lower arcuate portions adapted to receive opposed vertebral bone engaging screws, said implant being configured so that said bone screw receiving openings are adapted to be oriented towards the adjacent vertebral bodies in half rotation increments of said implant.

73. The implant of claim 60, wherein said trailing end is configured to cooperatively engage an implant driver.

74. The implant of claim 60, wherein said thread has peaks;
    said peaks being relatively constant along the length of said implant so that an outer diameter of said implant is generally constant.

75. The implant of claim 60, wherein said thread has a substantially constant height as measured from said upper and lower arcuate portions over a substantial portion of the length of said implant.

76. The implant of claim 60, wherein said thread is interrupted.

77. The implant of claim 60, wherein said thread is configured for linear advancement of said implant and requires an element of rotation to set said thread into the bone of the adjacent vertebral bodies.

78. The implant of claim 77, wherein said element of rotation is approximately 90 degrees.

79. The implant of claim 60, wherein said thread has a sharp pointed profile at said insertion end and progresses to a thicker and more squared profile at said trailing end.

80. The implant of claim 60, wherein said thread is a projection generally oriented perpendicular to the mid-longitudinal axis.

81. The implant of claim 60, wherein said thread forms a single helix.

82. The implant of claim 60, wherein said thread is one of a fin and a ridge.

83. The implant of claim 60, further comprising a hollow interior adapted to receive fusion-promoting substances.

84. The implant of claim 83, wherein at least one of said insertion and trailing ends is open to allow access to said hollow interior.

85. The implant of claim 60, wherein said upper and lower arcuate portions form at least a portion of a cylinder along the length of said implant.

86. The implant of claim 60, wherein said upper and lower arcuate portions form a generally frusto-conical shape.

87. The implant of claim 60, wherein said implant is tapered along a substantial portion of its length.

88. The implant of claim 60, wherein at least one of said upper and lower arcuate portions has a screw hole adapted to transmit a screw therethrough and into one of the vertebral bodies, said trailing end adapted to receive a screw therethrough and passing through a hollow interior of said implant and through said screw hole and Into one of the adjacent vertebral bodies.

89. The implant of claim 88, further comprising at least one screw adapted to pass from said hollow interior of said implant through said screw hole and into the adjacent vertebral body to anchor said implant to the adjacent vertebral body.

90. The implant of claim 60, wherein said trailing end is adapted to receive opposed bone screws and to transmit at least a portion of the screws through said upper and lower arcuate portions so as to engage at least one each into each of the vertebral bodies adjacent the disc space.

91. The implant of claim 60, wherein said trailing end includes opposed and divergently angled openings extending from said trailing end and through said upper and lower arcuate portions adapted to receive opposed vertebral bone engaging screws.

92. The implant of claim 88, wherein said trailing end includes retaining seats circumferentially around said screw hole adapted to receive and to block the passage of at least a portion of the screw to be inserted therethrough.

93. The implant of claim 88, wherein said trailing end is configured to cooperatively engage a lock for locking opposed bone screws to said implant.

94. The implant of claim 88, further including a lock for preventing backing out of bone screws from said implant.

95. The implant of claim 94, wherein the bone screws are lag screws and said lock allows for angular motion of the lag screws relative to said implant.

96. The implant of claim 95, wherein said lock is insertable into said implant.

97. The implant of claim 88, in combination with a bone screw.

98. The implant of claim 97, in combination with a lock for locking said bone screw.

99. The implant of claim 60, further comprising a cap for closing at least one of said ends of said implant, said cap having an exterior surface and an interior surface.

100. The implant of claim 99, wherein said interior surface of said cap has spaced slots about its circumference to facilitate a snap fit of said cap into said implant.

101. The implant of claim 99, wherein said cap includes a threaded portion for threadably engaging said insertion end of said implant.

102. The implant of claim 99, wherein said cap is perforated.

103. The implant of claim 60, wherein said implant comprises bone.

104. The implant of claim 103, wherein said bone includes cortical bone.

105. The implant of claim 60, wherein said implant comprises bone growth promoting material.

106. The implant of claim 105, wherein said bone growth promoting material is selected from one of bone morphogenetic protein, hydroxyapatite, and genes coding for the production of bone.

107. The implant of claim 60, wherein said implant is treated with a bone growth promoting substance.

108. The implant of claim 60, wherein said implant is a source of osteogenesis.

109. The implant of claim 60, wherein said implant is at least in part bioabsorbable.

110. The implant of claim 60, wherein said implant comprises a plastic material.

111. The implant of claim 60, wherein said implant comprises a ceramic material.

112. The implant of claim 60, wherein said implant is formed of a porous material.

113. The implant of claim 60, wherein said implant is formed of a material that intrinsically participates in the growth of bone from adjacent vertebral body to adjacent vertebral body through said implant.

114. The implant of claim 60, wherein said at least one opening is adapted to retain fusion-promoting materials.

115. The implant of claim 60, wherein at least a portion of said implant is treated to promote bone ingrowth between said implant and said adjacent vertebral bodies.

116. The implant of claim 60, in combination with a chemical substance to inhibit scar formation.

117. The implant of claim 60, wherein said implant comprises cancellously structured tantalum.

118. The implant of claim 60, wherein said characteristic and said starting point of said thread are coordinated to indicate a distinctive initial rotational orientation and insertion position of said implant to orient said upper and lower arcuate portions toward the adjacent vertebral bodies after rotation of said implant to a final installed position.

* * * * *

UNITED STATES PATENT AND TRADEMARK OFFICE
CERTIFICATE OF CORRECTION

PATENT NO. : 7,637,951 B2
APPLICATION NO. : 10246931
DATED : December 29, 2009
INVENTOR(S) : Gary K. Michelson It is certified that error appears in the above-identified patent and that said Letters Patent is hereby corrected as shown below:

Column 15:
Line 53: change "bane" to -- bone --.

Column 14:
Line 4: change "Into" to -- into --.

Signed and Sealed this

Twenty-third Day of March, 2010

David J. Kappos
*Director of the United States Patent and Trademark Office*